United States Patent [19]

Nickell

[11] 4,099,957

[45] Jul. 11, 1978

[54] RIPENING OF SUGARCANE BY USE OF ALCOHOLS

[75] Inventor: Louis G. Nickell, Ellicott City, Md.

[73] Assignee: W. R. Grace & Co., New York, N.Y.

[21] Appl. No.: 800,341

[22] Filed: May 25, 1977

[51] Int. Cl.$^2$ ............................................... A01N 9/24
[52] U.S. Cl. ..................................................... 71/122
[58] Field of Search ......................................... 71/122

[56] References Cited

U.S. PATENT DOCUMENTS 3,915,686  10/1975  Miller ..................................... 71/122

*Primary Examiner*—Catherine L. Mills
*Attorney, Agent, or Firm*—Philip M. Pippenger; William W. McDowell, Jr.

[57] ABSTRACT

Sucrose yield of sugarcane is increased by treating sugarcane a few weeks prior to harvest with isobutanol (2-methyl-1-hydroxypropane), n-propanol or ethyl alcohol as sugarcane ripening agents.

15 Claims, No Drawings

RIPENING OF SUGARCANE BY USE OF ALCOHOLS

CROSS-REFERENCE TO RELATED APPLICATION

Pending application Ser. No. 671,790 describes the use of ammonium isobutyrate as a ripening agent for sugarcane.

BACKGROUND OF THE INVENTION

Considerable progress has been made in the last several years in increasing the sugar yield of sugarcane by improving the varieties being planted, enriching the soil with fertilizers and irrigating the soil in climates which do not naturally provide sufficient moisture for optimum plant growth. More recent efforts in improving sugar production have increasingly turned toward the use of chemicals in modifying the controlling of the physiological processes of sugarcane, particularly in ripening prior to harvest. See U.S. Pat. Nos. 3,245,775; 3,291,592; 3,482,959; 3,482,961; 3,493,361; 3,505,056; 3,660,072; 3,671,219; 3,482,961; 3,870,503; 3,897,240; and 2,992,186 for example.

With some compounds previously suggested for this purpose, there has been some concern about their resistance to breakdown in the plant and their persistence in the soil when the intended use of the sugar is nutritive as opposed to industrial (e.g. in fermentation processes). Consequently, extensive efforts continue to be made in searching for effective chemical agents that can be used to modify the ripening of sugarcane so as to increase the sucrose yield therefrom.

Generally speaking, chemicals selected for evaluation have been of types which have been previously found active in work with other plants as plant hormones, herbicides or inhibitors of growth of terminal buds, or active in killing the spindle of cane upon topical microapplication, etc. However, among the compounds heretofore found to be useful for such other special purposes, surprisingly few have been found effective in controlling the ripening of sugarcane in the desirable manner. No predictable relationship has been recognized to date between (a) the chemical structure of such compounds, (b) their phytotoxic effects, or (c) their physiological effects on the morphogenetic development of the plant, and their activity in having positive effects on ripening. In other words, the effectiveness of a compound in controlling the ripening of sugarcane and thereby increasing sugar yield remains essentially unpredictable, and the search for suitable agents continues to be fundamentally empirical.

Isobutyrate salts of Group 1 of the Periodic Table and isobutyrate ethyl esters are known as sugarcane ripening agents. See. L. G. Nickell, U.S. Pat. No. 3,870,503 and application Ser. No. 671,790 referenced above. However, isobutanol, n-propanol and ethyl alcohol for this use are believed novel and unpredictable.

OBJECTS OF THE INVENTION

It is an object of this invention to provide a new agent for controlling the ripening of sugarcane. A more specific object is to increase the sucrose yield of sugarcane by chemically treating it during its final ripening stages prior to harvest without introducing substantial toxicological hazards, and preferably without causing any visible damage to the cane plant such as drying of the spindle or other leaf.

Still more specifically, it is an object to increase the sucrose yield of sugarcane by treating it prior to harvest with a chemical agent which is sufficiently stable to provide the desired effect over a period of several weeks and thus give adequate operational flexibility, but which has a relatively low degree of persistence and is susceptible to autodecomposition or decomposition by soil bacteria. Compounds which increase the sucrose content of sugarcane only temporarily over a period of 2 or 3 weeks after application and then result in a substantial decrease are generally not desirable for the intended purpose.

SUMMARY OF THE INVENTION

It has now been discovered that excellent results in increasing the sucrose yield of sugarcane can be obtained by applying isobutanol as a sugarcane ripening agent to the cane at a time at least about 2 weeks and up to about 10 weeks before harvest. Ethyl alcohol and n-propanol can be similarly employed. While the following description of the invention is related to isobutanol, the description including ranges employed and time of application relates to ethyl alcohol and n-propanol as well.

DESCRIPTION OF SPECIFIC EMBODIMENTS

Isobutanol is a water-soluble liquid under normal ambient conditions. This sugarcane ripening agent is generally applied to the sugarcane in an aqueous solution.

Good results are obtained when the sugarcane crop is treated at a rate in the range of from about 1 to about 40 pounds of isobutanol per acre of sugarcane, though higher rates of up to about 80 pounds or more per acre as well as rates lower than 1 pound per acre can be used. The optimum amount will vary somewhat depending on the specific treating composition applied.

In accordance with this invention, the sugarcane crop is treated with the sugarcane ripening agent at any time from 2 to 10 weeks before harvest, the preferred time for treatment being between about 3 and 8 weeks prior to harvest.

The sugarcane ripening agent is conveniently applied to the field in the form of an aqueous solution or suspension, e.g. a liquid composition which may be sprayed from a boom-spray or a solid dust composition where the active compound is adsorbed onto an inert solid such as clay and which can be applied as a dust from an airplane.

With the type of boom-spray apparatus used in this work, it is convenient to apply the active ingredient to the sugarcane field in the form of an aqueous solution having a concentration of active agent such that the application at a rate of from 5 to 20 gallons of liquid composition per acre will provide the required dosage of active chemical. However, the use of lower or higher amounts may be preferred when a different dispensing mechanism is used.

Water is the preferred liquid carrier for isobutanol in practicing the present invention. Instead of using water as the carrier, nonphytotoxic mineral oils either as such or in the form of water-in-oil or oil-in-water emulsions may be used similarly in accordance with practices which are common in the art of treating vegetation with beneficial growth control agents. Other active ingredients are not required with the isobutanol being present as essentially the sole active ingredient in the solution or suspension.

The invention is additionally illustrated in connection with the following Examples which are to be considered as illustrative of the present invention. It should be understood, however, that the invention is not limited to the specific details of the Examples.

EXAMPLE 1

A 0.3 ml. dose of aqueous solution containing 38 mg. of isobutanol (equivalent to 4 lbs. of isobutanol/acre) was applied on the spindle area of each of 30 stalks of sugarcane in a commercial field in Hawaii, using a syringe with a fine needle as the applicator. Another group of 30 stalks in the same test were treated at the rate of 0.06 ml/stalk which is 76 mg./stalk and is equivalent to 8 lbs/acre. The age of the cane at the time of application was 21.5 months.

A set of 10 of these treated stalks from each group was harvested at 4 weeks after such treatment and other sets of 10 were harvested at 5 and 6 weeks following treatment. In each harvest a set of 10 untreated stalks were also harvested as a control.

The top 15 joints of the treated cane as well as those of similar untreated cane (control) are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugarcane.

The results are given in Table I below.

EXAMPLE 2

In a similar manner to Example 1, isobutanol was tested against n-butanol and 2-ethyl hexanol. The results are set forth in Table II. At the 4 week harvest both n-butanol and 2-ethylhexanol appear to have depressed ripening. At both the 4 and 5 week harvests isobutanol resulted in a substantial improvement in juice purity and pol percent cane.

TABLE II

| | Time from Treatment to Harvest | | | |
|---|---|---|---|---|
| | 4 Weeks | | 5 Weeks | |
| Compound | Juice Purity | Pol % Cane | Juice Purity | Pol % Cane |
| Isobutanol (4 lbs./acre) | 72.45 | 7.80 | 84.27 | 12.83 |
| n-butanol (4 lbs./acre) | 55.99 | 5.73 | 62.37 | 6.24 |
| 2-ethyl hexanol (4 lbs./acre) | 69.84 | 7.77 | 73.55 | 9.11 |
| Control (untreated) | 72.72 | 8.66 | 76.74 | 9.76 |

EXAMPLE 3

In a manner similar to Example 1, isobutanol was compared with several alcohols. The results are set forth in Table III. It is apparent that isobutanol was clearly superior to the control. At the five week harvest, the isobutanol was superior to methanol and isopropanol but appeared to be less active than ethanol and n-propanol.

TABLE III

| | Time from Treatment to Harvest | | | |
|---|---|---|---|---|
| | 4 Weeks | | 5 Weeks | |
| Compound | Juice Purity | Pol % Cane | Juice Purity | Pol % Cane |
| Isobutanol (4 lbs./acre) | 77.13 | 8.26 | 80.39 | 9.86 |
| Methanol (4 lbs./acre) | 78.29 | 8.96 | 75.71 | 8.53 |
| Ethanol (4 lbs./acre) | 79.63 | 9.60 | 80.61 | 10.32 |
| Isopropanol (4 lbs./acre) | 80.38 | 9.75 | 72.29 | 7.50 |
| n-propanol (4 lbs./acre) | 79.58 | 10.09 | 83.93 | 11.25 |
| Control (untreated) | 76.60 | 8.67 | 74.83 | 8.18 |

What is claimed is:

1. A process for increasing the sugar yield of grown sugarcane which comprises applying an effective amount of isobutanol as a sugarcane ripening agent to the cane at a time at least about 2 and up to about 10 weeks prior to harvest.

2. A process according to claim 1 wherein said sugarcane ripening agent is applied to the cane at a rate corresponding to from about 1 to about 80 pounds per acre.

3. A process according to claim 1 wherein the com-

TABLE I

| | Time From Treatment to Harvest | | | | | |
|---|---|---|---|---|---|---|
| | 4 Weeks | | 5 Weeks | | 6 Weeks | |
| Compound | Juice Purity | Pol % Cane | Juice Purity | Pol % Cane | Juice Purity | Pol % Cane |
| Isobutanol (4 lbs./acre) | 63.37 | 6.86 | 76.99 | 9.21 | 80.92 | 11.77 |
| Isobutanol (8 lbs./acre) | 61.44 | 6.28 | 80.21 | 10.69 | 76.01 | 9.77 |
| Control (untreated) | 70.03 | 8.29 | 73.65 | 9.15 | 73.60 | 8.80 |

As is apparent, after 5 and 6 weeks the application of isobutanol results in a substantial improvement in both juice purity and pol percent cane.

pound is applied to the cane at a time of between about 3 and about 8 weeks before harvest.

4. A process according to claim 2 wherein said sugarcane ripening agent is applied to the cane at a rate corresponding to from about 1 to about 40 pounds per acre.

5. A process according to claim 1 wherein the sugarcane ripening agent is applied to the cane at a rate of from 1 to about 40 pounds per acre and at a time of between about 3 and about 8 weeks before harvest.

6. A process for increasing the sugar yield of grown sugarcane which comprises applying an effective amount of ethyl alcohol as a sugarcane ripening agent to the cane at from about 2 up to about 10 weeks prior to harvest.

7. A process for increasing the sugar yield of grown sugarcane which comprises applying an effective amount of n-propanol as a sugarcane ripening agent to the cane at from about 2 up to about 10 weeks prior to harvest.

8. A process according to claim 6 wherein said sugarcane ripening agent is applied to the cane at a rate corresponding to from about 1 to about 80 pounds per acre.

9. A process according to claim 6 wherein the compound is applied to the cane at a time of between about 3 and about 8 weeks before harvest.

10. A process according to claim 6 wherein said sugarcane ripening agent is applied to the cane at a rate corresponding to from about 1 to about 40 pounds per acre.

11. A process according to claim 6 wherein the sugarcane ripening agent is applied to the cane at a rate of from 1 to about 40 pounds per acre and at a time of between about 3 and about 8 weeks before harvest.

12. A process according to claim 7 wherein said sugarcane ripening agent is applied to the cane at a rate corresponding to from about 1 to about 80 pounds per acre.

13. A process according to claim 7 wherein the compound is applied to the cane at a time of between about 3 and about 8 weeks before harvest.

14. A process according to claim 7 wherein said sugarcane ripening agent is applied to the cane at a rate corresponding to from about 1 to about 40 pounds per acre.

15. A process according to claim 7 wherein the sugarcane ripening agent is applied to the cane at a rate of from 1 to about 40 pounds per acre and at a time of between about 3 and about 8 weeks before harvest.

* * * * *